United States Patent [19]

Dyck et al.

[11] Patent Number: 4,576,156

[45] Date of Patent: Mar. 18, 1986

[54] PROPHYLACTIC DEVICE AND METHOD

[75] Inventors: Manfred F. Dyck, Somerville; Walter A. Haine, Bridgewater, both of N.J.

[73] Assignee: Ortho Pharmaceutical Corporation, Raritan, N.J.

[21] Appl. No.: 896,844

[22] Filed: Apr. 17, 1978

[51] Int. Cl.$^4$ ............ A61B 19/00; B29D 51/00
[52] U.S. Cl. .................. 128/132 R; 128/132 D; 128/138 R; 264/320
[58] Field of Search ............ 128/132, 294, 138; 560/157; 264/101, 292, 320, 322; 528/73

[56] References Cited

U.S. PATENT DOCUMENTS

| | | | |
|---|---|---|---|
| 1,853,016 | 4/1932 | De Laney | 264/320 |
| 1,935,165 | 11/1933 | Steinle | 264/101 |
| 2,199,790 | 5/1940 | Guinzburg | 264/320 |
| 2,371,883 | 3/1945 | Gammeter et al. | 128/294 |
| 2,625,535 | 1/1953 | Mastin et al. | |
| 3,004,591 | 1/1977 | Freimark | 128/294 |
| 3,020,596 | 2/1962 | Clapp et al. | 264/322 |
| 3,128,762 | 4/1964 | Young | 128/127 |
| 3,363,624 | 1/1968 | Fishman | 128/132 |
| 3,486,968 | 12/1969 | Mater | 128/132 R |
| 3,496,938 | 2/1970 | Furuse | 128/271 |
| 3,563,244 | 2/1971 | Aska et al. | 128/294 |
| 3,809,090 | 5/1974 | Povlacs et al. | 128/294 |
| 4,049,591 | 9/1977 | McEntire et al. | 560/157 |
| 4,085,177 | 4/1977 | Sauer | 264/89 |
| 4,119,094 | 10/1978 | Micklus et al. | 128/294 |
| 4,123,589 | 10/1978 | Korlatzki et al. | 528/73 |

FOREIGN PATENT DOCUMENTS 1259284 1/1972 United Kingdom .
1509816 5/1978 United Kingdom .

OTHER PUBLICATIONS

"Structure & Properties of Rubbers", *The Nature & Properties of Engr. Materials*, Jastrzebski, Table A5, Wiley.
*Websters Seventh New Collegiate Dictionary*, Merriam Co., p. 917.
"Thermoplastic Processing Rubbers", *Handbook of Common Polymers*, CRC, 1973, p. 3.
Kirk-Othmer, "Ferroelectrics to Foams", Encyclopedia of Chemical Technology, vol. 9, Interscience Publishers, NY, p. 232 et seq. ('67).

*Primary Examiner*—Thomas Wallen
*Attorney, Agent, or Firm*—Lawrence D. Schuler

[57] ABSTRACT

A prophylactic or contraceptive device made from a thermoplastic polyurethane material having a generally cylindrical configuration with a closed end.

7 Claims, 1 Drawing Figure

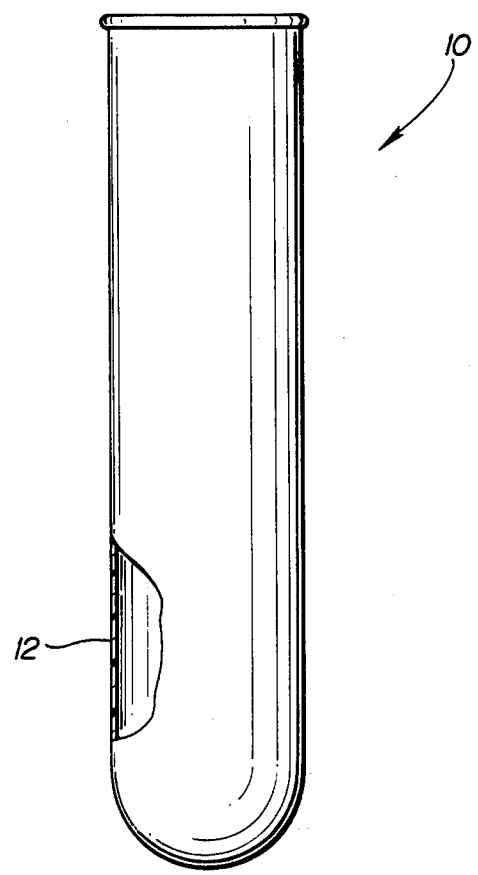

PROPHYLACTIC DEVICE AND METHOD

This invention relates to prophylactic devices of the type normally employed to prevent infection, the transmission of diseases, and venereal diseases in particular, and for purposes of birth control. As employed herein, the term prophylactic device is intended to include not only prophylactics which are used to prevent venereal infection but also devices which can be worn over extremities or parts thereof for the prevention of or protection against infection and disease. Such devices are generally prepared from a rubber type material in the form of a thin, tubular membrane one end of which is closed and they effect the desired result by the formation of a mechanical barrier around the external body member it is designed to protect. In order to allow the protected body member to move freely and to respond to external stimulation during use, it is necessary to make the devices from very thin materials. However, because of the thinness of the material employed, these devices must be manufactured and tested with great care in order to assure against leakage due to the presence of small holes or perforations in the device.

Prophylactic devices of the type to which the present invention relates may be broadly described as elongated elastic tubular sheaths or cylinders which are adapted to fit closely on the body member to be protected. They are generally made from rubber like materials in thin pellicles or membranes. While thinness is generally desirable for minimizing impairment of movement, sensation and feeling of the protected member during use it has proven to be disadvantageous and detrimental under certain circumstances. Devices which are too thin often develop pinholes during manufacture and sometimes leak or rupture during use. There is a need, therefore, for a prophylactic or protective device which is thin enough so as not to impair movement or feeling in the protected member but still strong enough to prevent the formation of pinholes during manufacture or rupture or leakage during use. We have found that such devices when made from thermoplastic polyurethanes have all of the above advantages but none of the disadvantages associated with the prior art devices.

It is one object of the present invention to provide a method of preparing a pinhole free prophylactic or protective device from thermoplastic polyurethanes.

It is another object of this invention to provide an improved prophylactic or protective device which is pinhole free, thin enough so as not to impair sensation or movement of the body member, but strong enough so as not to rupture during use.

A further object of the invention is the provision of a device which may be readily and economically manufactured and which may be conveniently packaged and stored indefinitely while being available for immediate use.

These and other objects of the invention will be apparent from the description of the preferred embodiments below.

FIG. 1 is an elevational view, with a portion shown in section, of a prophylactic device 10 of the type claimed herein, comprising elastomeric thermoplastic polyurethane 12.

The prophylactic devices currently available are generally made from either natural materials such as rubber and animal membranes or synthetic materials such as rubber latex. Other materials such as neoprene, polyethylene or polyvinyl chloride have also been employed. Rubber latex is the most widely used material but fabrication of the device from this material is cumbersome due to the long dip-coating and drying process which must be employed. In addition, the latex devices have a limited shelf life since the material itself is relatively unstable and degrades gradually on standing.

Attempts have been made to prepare prophylactic devices from certain polyurethanes but to date none has been successful. Past attempts at making polyurethane devices have all centered around the use of a dip-coating technique employing either two-component polyurethanes, which results in a crosslinked polyurethane, or by using solvent solutions of polyurethanes which are dip-coated on mandrils after which the solvent mixture is removed. However, all of these techniques have inherent disadvantages. In the solvent solution method, for example, removal of the solvent is difficult and expensive and residual solvents are often very toxic. In the dip-coating process, one must contend with the problem of removing the air which, if left behind, will result in a porous device. The net result is then a high rejection rate due either to membrane porosity or non-uniform casting of the membrane.

The prophylatic device of the present invention consists of an elongated, elastic sheath or cylinder which is adapted to fit closely on the body member to be protected. The device is made from a thin pellicle or membrane of a thermoplastic polyurethane having a thickness of about 0.01 mm, or less, to about 0.25 mm. The preferred thickness is between about 0.01 mm and 0.02 mm. Prior to the present invention, thermoplastic polyurethanes have not been employed in the making of prophylactic devices. Thermoplastic polyurethanes are desirable materials because of their inherent biocompatibility, smoothness and strength.

Any thermoplastic polyurethane may be employed to form the films used to prepare the prophylactic device of the present invention. However, in order to achieve a certain degree of softness and flexibility, it is preferred to use thermoplastic polyurethanes having an average Shore A hardness of about 50 to about 90. The most preferred range is from about 75 to 90. The tensile stress of the thermoplastic polyurethane at 100% elongation, commonly referred to as the 100% modulus, should be between about 300 and 1000 psi. At 300% elongation the tensile stress should be between about 800 and 3000 psi. In a preferred embodiment of the invention, at 100% elongation the tensile stress should be between 400 and 800 psi and at 300% it should be between 800 and 2500 psi. The tensile strength should be about 4000 to about 8000 psi while the permanent set should be less than 25%. Suitable thermoplastic polyurethanes which can be employed to prepare the prophylactic devices of this invention include polytetramethylene ether glycol-diphenylmethane diisocyanate (MDI), polytetramethylene ether glycol-toluene diisocyanate (TDI), polytetramethylene ether glycol-isoferrone isocyanate, poly (1,4-oxybutylene) glycol-diphenylmethane diisocyanate (MDI), poly (1,4-oxybutylene) glycol-toluene diisocyanate (TDI), poly (1,4-oxybutylene) glycol-isoferrone isocyanate, polyethylene glycol-diphenylmethane diisocyanate (MDI), polyethylene glycol-toluene diisocyanate (TDI), polyethylene glycol-isoferrone isocyanate, polypropylene glycol-diphenylmethane diisocyanate (MDI), polypropylene glycol-toluene diisocyanate (TDI), polypropylene glycol-isoferrone isocyanate, polycaprolactonediphenylmethane diisocyanate (MDI), polycaprolactonetoluene diisocyanate (TDI), polycaprolactone-isoferrone isocyanate, polyethylene adipate-diphenylmethane diisocyanate (MDI), polyethylene adipate-toluene diisocyanate (TDI), polyethylene adipate-isoferrone isocyanate, polytetramethylene adipate-diphenylmethane diisocyanate (MDI), polytetramethylene adipate-toluene diisocyanate (TDI), polytetramethylene adipate-isoferrone isocyanate, polyethylenepropylene adipate-diphenylmethane diisocyanate (MDI), polyethylene-propylene adipatetoluene diisocyanate (TDI), and polyethylene-propylene adipate-isoferrone isocyanate polyurethanes. The preferred polyurethanes are the polyether or polyester based urethane elastomers. Blends of different polyurethanes may be employed to obtain films having the desired physical characteristics. The addition of plasticizers and other additives known to those skilled in the art during preparation of the polyurethane films is also comtemplated.

Thermoplastic polyurethanes have been found to be superior to the prior art materials in physical strength. Films made from thermoplastic polyurethanes exhibit superior abrasion resistance and tear resistance properties and have greater tensile strength than the prior art materials. In addition, the thermoplastic polyurethanes generally do not show a significant amount of absorption of materials like body enzymes or other proteins; these are properties which make them more desirable materials for the preparation of prophylactic devices.

The prophylactic devices of the present invention are generally prepared from extruded films of the thermoplastic polyurethane preferably cut into small units. For example, in the preparation of a prophylactic, or condom, it is preferred to use 6 inch squares of the polyurethane although larger and smaller units may be employed depending upon the particular size device desired. In a typical process, the thermoplastic polyurethane is heated prior to contacting it with a preformed mandril to a temperature high enough to soften the polymer but low enough to prevent chemical degradation. The film is generally preheated, preferably in a clamping frame, to a temperature of about 400°–500° F. The heated film and mandril are then brought into intimate contact causing the film to assume the shape of the mandril. Mandrils of varying sizes and shapes may be employed; the particular size and shape mandril employed in a given instance will depend on the size and shape of the device desired. During the period when the device is actually being formed, it is preferred to apply a vacuum to the system in order to bring about uniformity in wall thickness. The use of a vacuum results in a device having greater elasticity and ensures the formation of a pinhole free device. These characteristics are particularly noticeable in the tip section of the device. The vacuum forming technique in itself requires the absolute absence of any pinholes since the film would collapse if pinholes were present. When vacuum is employed as part of the process, the entire procedure is carried out in a vacuum forming machine. The vacuum applied during the forming step is generally between about 1 and about 12 inches of mercury. The maximum vacuum to be applied is about 15 inches of mercury. The mold temperature is generally maintained between about 400°–500° F. during the operation. A cycle time of about 15–25 seconds for preheating the film and about 10–100 seconds for set-up time prior to separation of the device from the mandril is generally employed. The temperature and time employed in the molding step are not critical. The particular temperature range and cycle time employed, however, will depend upon the particular thermoplastic polyurethane employed and the time allowed for the polyurethane to set. The cycle time from preheating the film to separation of the device from the mandril will vary according to the particular temperatures employed and the efficiency with which the mandril is cooled.

The same polyurethane materials and procedure can be employed to make other prophylactic protective devices, such as finger cots, wherein walls strong enough to resist rupture during use but still thin enough so as not to seriously impair movement, sensation and feeling are desired. In the case of the finger cots, for example, they can be prepared in the same manner as the condom except that a mandril fashioned in the shape of a human finger is employed. Such devices are considered to be part of the present invention and are included in the generic term prophylactic device.

The following procedure illustrates the process for making a prophylactic device from a thermoplastic polyurethane.

The extruded polyurethane film (Pellethane* x5036–80AA is cut into a six inch square, clamped on a clamping frame and heated at 460° F. for 18–20 seconds. The film is placed in a vacuum chamber. Vacuum is applied (12 inches mercury) and the mandril (10 inches) is moved downward into the film. As the mandril moves into the film, the vacuum in the chamber is shut off. Once the mandril is moved down completely, vacuum is applied at the base of the mandril which pulls the film down tightly causing it to assume the form of the mandril. The parts are held in place for 30–100 seconds after which the vacuum is released. The excess material at the base is cut off and the film is partly rolled up onto itself for a distance of about 3 inches. The remaining portion of the device is dusted with powder and the film is rolled up until it can be removed easily from the mandril.

*An Upjohn polyether based urethane elastoplastic polymer.

Preferred embodiments of this invention have been described in the foregoing specification, but it is specifically contemplated that modifications thereof and additions thereto will be obvious to those skilled in the art and such modifications and additions are specifically contemplated as being part of this invention, the scope of which is limited only as defined in the appended claims.

What is claimed is:

1. The method of preparing a prophylactic device comprising a thin body of substantially homogeneous elastomeric theremoplastic polyurethane material having a substantially cylindrical principal portion which is closed at one end, said cylindrical portion providing a wall of substantially uniform thickness, which method comprises deforming a sheet of a thermoplastic polyurethane elastomer with a preformed mandril at an elevated temperature, whereby said polyurethane elastomer assumes the shape of said mandril forming a polyurethane prophylactic device having a substantially cylindrical principal portion and a wall of substantially uniform thickness.

2. The method of claim 1 wherein a vacuum is applied to the system during the deformational step.

3. The method of claim 2 wherein the deformational step is carried out at a temperature between 400°–500° F.

4. The method of claim 2 wherein the applied vacuum is between about 1 and 12 inches of mercury.

5. The method of claim 1 wherein the thermoplastic polyurethane is a polyether or polyester based urethane elastomer.

6. The method of claim 1 wherein the prophylactic device is in the shape of a condom.

7. The method of claim 1 wherein the prophylactic device is in the shape of a finger cot.

* * * * *